(12) United States Patent
Tokiwa

(10) Patent No.: US 11,009,519 B2
(45) Date of Patent: May 18, 2021

(54) AUTOMATED ANALYZER AND IMAGE PROCESSING METHOD

(71) Applicant: Hitachi High-Technologies Corporation, Tokyo (JP)

(72) Inventor: Koji Tokiwa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 16/626,413

(22) PCT Filed: Jun. 7, 2018

(86) PCT No.: PCT/JP2018/021804
§ 371 (c)(1),
(2) Date: Dec. 24, 2019

(87) PCT Pub. No.: WO2019/021645
PCT Pub. Date: Jan. 31, 2019

(65) Prior Publication Data
US 2020/0141960 A1 May 7, 2020

(30) Foreign Application Priority Data

Jul. 25, 2017 (JP) .............................. JP2017-143993

(51) Int. Cl.
*G01N 35/04* (2006.01)
*G01N 21/17* (2006.01)
*G01N 33/86* (2006.01)

(52) U.S. Cl.
CPC ............. *G01N 35/04* (2013.01); *G01N 21/17* (2013.01); *G01N 33/86* (2013.01); *G01N 2035/0439* (2013.01); *G01N 2201/064* (2013.01)

(58) Field of Classification Search
None
See application file for complete search history.

(56) References Cited

U.S. PATENT DOCUMENTS

2008/0240984 A1  10/2008  Wakamiya et al.
2009/0214385 A1  8/2009  Mori et al.
(Continued)

FOREIGN PATENT DOCUMENTS

CN   101520465 A   9/2009
CN   102023225 A   4/2011
(Continued)

OTHER PUBLICATIONS

Chinese-language Office Action issued in Chinese Application No. 201880047513.4 dated May 15, 2020 with EnglishTranslation (22 pages).

(Continued)

*Primary Examiner* — Kathryn Wright
(74) *Attorney, Agent, or Firm* — Crowell & Moring LLP

(57) ABSTRACT

This automated analyzer comprises: a sample disk for mounting sample containers accommodating samples; a sample disk control unit for controlling the rotation of the sample disk; a sample dispensing probe for sucking the sample out of a sample container that has arrived at a prescribed suction position as a result of the rotation of the sample disk; a photometer for carrying out automatic biochemical analysis; a blood coagulation time detection unit for carrying out blood coagulation time analysis; a light-blocking cover that covers the photometer and blood coagulation time detection unit; and a sample information output unit for outputting sample information. The sample information output unit acquires analysis information indicating the analysis state of the mounted samples and position information indicating the positions of the samples as sample disk monitor information 401 and displays the analysis information, the position information, and an image 402 showing the light-blocking cover on the imaging unit so as to overlap.

4 Claims, 6 Drawing Sheets

(56) References Cited

U.S. PATENT DOCUMENTS

| | | |
|---|---|---|
| 2010/0114501 A1 | 5/2010 | Kondou et al. |
| 2016/0274133 A1* | 9/2016 | Yabutani .......... G01N 35/00584 |
| 2017/0212138 A1 | 7/2017 | Sakai et al. |
| 2018/0275155 A1 | 9/2018 | Matsuoka et al. |
| 2019/0011471 A1 | 1/2019 | Abe |

FOREIGN PATENT DOCUMENTS

| | | | |
|---|---|---|---|
| CN | 106170702 A | 11/2016 | |
| CN | 106662593 A | 5/2017 | |
| JP | 5-72215 A | 3/1993 | |
| JP | 2007-315970 A | 12/2007 | |
| JP | 2008-241670 A | 10/2008 | |
| JP | 2010-107433 A | 5/2010 | |
| JP | 2016-211948 A | 12/2016 | |
| JP | 2017-116472 A | 6/2017 | |
| WO | WO-2016017289 A1 * | 2/2016 | ........... G01N 35/025 |
| WO | WO 2017/122455 A1 | 7/2017 | |

OTHER PUBLICATIONS

International Search Report (PCT/ISA/210) issued in PCT Application No. PCT/JP2018/021804 dated Sep. 11, 2018 with English translation (two (2) pages).

Japanese-language Written Opinion (PCT/ISA/237) issued in PCT Application No. PCT/JP2018/021804 dated Sep. 11, 2018 (four (4)pages).

English translation of document C2 (Japanese-language Written Opinion (PCT/ISA/237) previously filed on Dec. 24, 2019) issued in PCT Application No. PCT/JP2018/021804 dated Sep. 11, 2018 (five (5) pages).

* cited by examiner

Fig. 4
| SAMPLE DISK | SAMPLE DISK MONITOR INFORMATION |
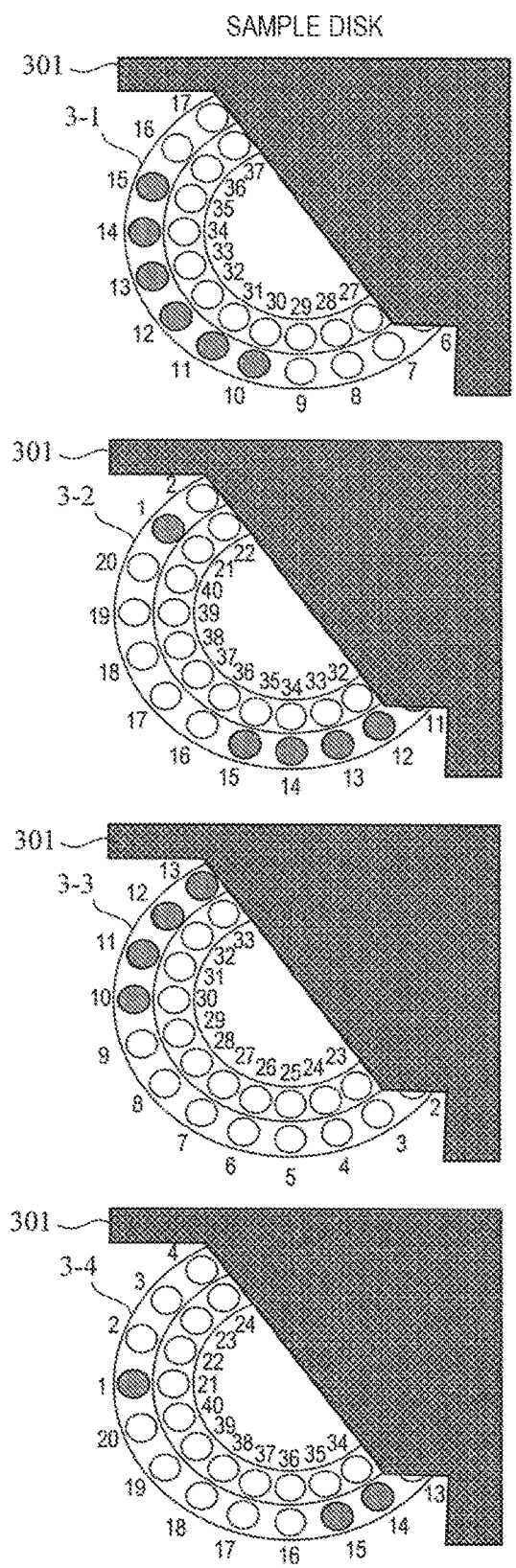
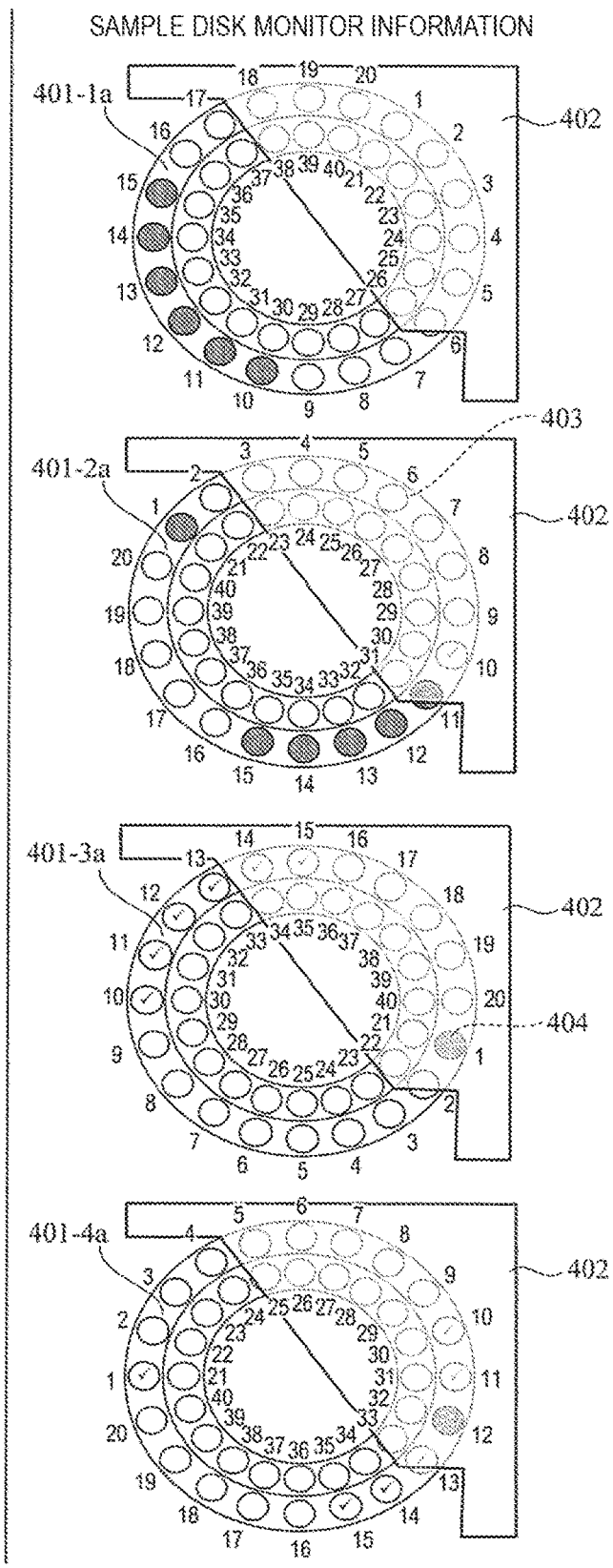

AUTOMATED ANALYZER AND IMAGE PROCESSING METHOD

TECHNICAL FIELD

The present invention relates to an automatic analyzer that analyzes a biological sample, and an image processing method thereof.

BACKGROUND ART

Automatic analyzers that analyze analyte samples such as blood and urine qualitatively and/or quantitatively have been known. Some of the automatic analyzers include a display unit, and the display unit displays position information, a management number, an analysis result, and the like of an analyte placed on a sample disk as sample disk monitor information.

Since the sample disk monitor information is displayed with status of the analyte samples being updated while analysis of the analyte is in progress, a user of the automatic analyzer can easily grasp the status of all the analyte samples based on the information.

PTL 1 discloses an automatic analyzer that includes an actual turntable formed such that a plurality of containers into which an analyte is injected can be arranged thereon in a circumferential direction, and that displays a virtual turn table in an annular shape together with numbers indicating positions of the containers arranged on the actual turntable and numbers of times of measurement of the analyte injected into the containers.

CITATION LIST

Patent Literature

PTL 1: JP-A-2016-211948

SUMMARY OF INVENTION

Technical Problem

In general, an automatic analyzer often includes a photometer that measures scattered light and transmitted light of light irradiated to an analyte and a detector that performs blood coagulation time analysis. The detector is covered by a light shielding cover so that unnecessary light which causes a decrease in observation accuracy does not enter.

The light shielding cover covers not only the detector but also a part of a sample disk on which the analyte is placed. Therefore, when an analyte sample container placed on the sample disk is to be replaced, it is required to rotate the sample disk until the analyte sample container comes to an area where the analyte sample container is not positioned below the light shielding cover. That is, it is required for a user to place the analyte sample container on the sample disk or remove the analyte sample container from the sample disk, in an area not covered by the light shielding cover of the sample disk.

However, the automatic analyzer described in PTL 1 does not display on a display unit whether an analyte sample container is in a state of being ready to be removed from the actual turntable or in a state of being ready to be placed thereon. Therefore, in a case of the automatic analyzer described in PTL 1, it is required for the user to repeatedly place the analyte sample container or remove the analyte sample container in accordance with an operating state of the automatic analyzer, which is inconvenient for continuous utilization of the automatic analyzer.

The invention has been made in view of the above circumstances, and provides a technique capable of easily determining placement and removal of an analyte sample container with respect to an automatic analyzer.

Solution to Problem

To solve the above problems, the invention provides an automatic analyzer that includes: a sample disk on which an analyte sample container containing an analyte sample is to be placed; a sample disk control unit configured to control rotation of the sample disk; a sample dispensing probe configured to aspirate the analyte sample from the analyte sample container when the analyte sample container reaches a predetermined aspirating position by rotation of the sample disk; a photometer configured to perform automatic biochemical analysis; a blood coagulation time detection unit configured to perform blood coagulation time analysis; a light shielding cover configured to cover the photometer and the blood coagulation time detection unit; and a sample information output unit configured to output information on the analyte sample, in which the sample information output unit is configured to acquire analysis information indicating an analysis state of the analyte sample placed on the sample disk and position information indicating a position of the analyte sample, and to display the analysis information, the position information, and an image showing the light shielding cover on a display unit in a manner superimposed on one another.

Further, the invention provides an image processing method of an automatic analyzer, in which the automatic analyzer includes: a sample disk on which an analyte sample container containing an analyte sample is to be placed; a sample disk control unit configured to control rotation of the sample disk; a sample dispensing probe configured to aspirate the analyte sample from the analyte sample container when the analyte sample container reaches a predetermined aspirating position by rotation of the sample disk; a photometer configured to perform automatic biochemical analysis; a blood coagulation time detection unit configured to perform blood coagulation time analysis; and a light shielding cover configured to cover the photometer and the blood coagulation time detection unit, and in which the image processing method comprises: a step of acquiring analysis information indicating an analysis state of the analyte sample placed on the sample disk and position information indicating a position of the analyte sample; and a step of displaying the analysis information, the position information, and an image indicating the light shielding cover on a display unit in a manner superimposed on one another.

This application is based upon and claims the benefit of priority from Japanese Patent Application No. 2017-143993, the entire contents of which are incorporated herein by reference.

Advantageous Effect

According to the invention, placement and removal of an analyte sample container can be easily determined. Problems, configurations, and effects other than those described above will be further clarified with the following description of embodiments.

BRIEF DESCRIPTION OF DRAWINGS

FIG. 4 is a diagram illustrating changes of a sample disk and sample disk monitor information.

DESCRIPTION OF EMBODIMENTS

Figure 1:
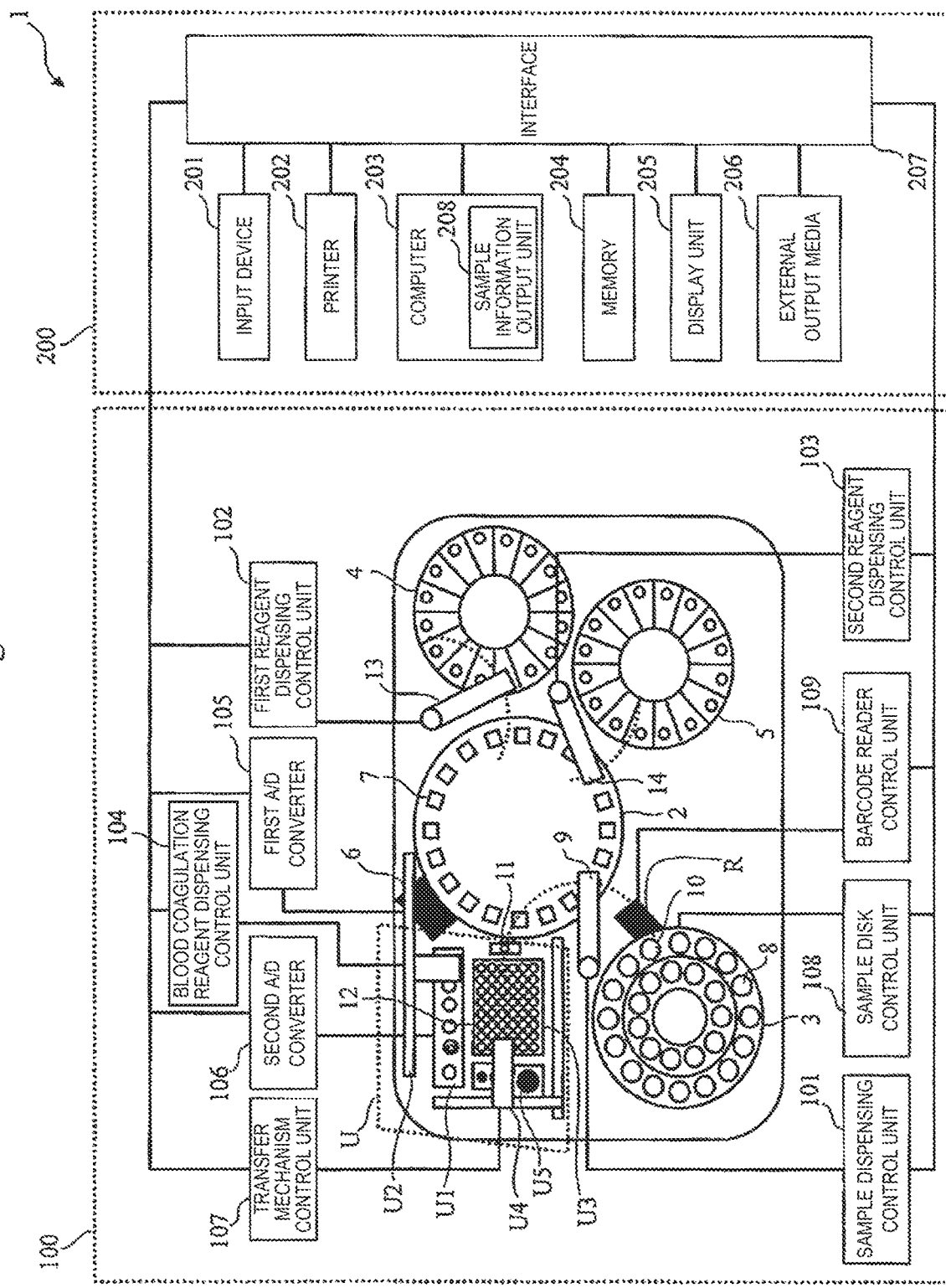
FIG. 1 is a diagram illustrating an overall configuration of an automatic analyzer according to an embodiment.

Hereinafter, embodiments of the invention will be described with reference to the drawings. The embodiments of the invention are not limited to the embodiments to be described below, and various modifications can be made within the scope of the technical idea thereof. Corresponding parts of the drawings used in the description of the embodiments to be described below are denoted by the same reference numerals, and a repetitive description thereof will be omitted.

Embodiments

[Configuration of Automatic Analyzer]

FIG. 1 is a diagram illustrating an overall configuration of an automatic analyzer 1 according to an embodiment. Here, as an aspect of the automatic analyzer 1, an example of a complex automatic analyzer 1, which includes a turntable type biochemical analysis unit 100 and an operation unit 200, will be described.

As illustrated in FIG. 1, a reaction disk 2, a sample disk 3, a first reagent disk 4, a second reagent disk 5, a blood coagulation time analysis unit U, and a photometer 6 are disposed on a casing of the automatic analyzer 1. A barcode reader R is attached to the sample disk 3.

The reaction disk 2 is a disk-shaped unit that is rotatable clockwise or counterclockwise, and is configured such that a plurality of reaction containers 7 can be arranged on a circumference thereof.

The sample disk 3 is a disk-shaped unit that is rotatable clockwise or counterclockwise, and is configured such that a plurality of analyte sample containers 8 containing samples, such as a standard sample or an examination sample, can be arranged on a circumference thereof.

The first reagent disk 4 and the second reagent disk 5 are disk-shaped units that are rotatable clockwise or counterclockwise, and are configured such that a plurality of reagent containers containing a reagent can be arranged on circumferences thereof. The reagent contains a component that reacts with components of examination items contained in the sample. Although not illustrated in FIG. 1, the first reagent disk 4 and the second reagent disk 5 can include a cold-insulation mechanism so as to be configured to be capable of performing cold-insulation of the reagent in the arranged reagent container.

A sample dispensing probe 9 is disposed between the sample disk 3 and the reaction disk 2. The sample dispensing probe 9 can rotate about an axis thereof, and an aspirating position and a dispensing position of the sample are present on a rotation orbit thereof.

The sample dispensing probe 9 can aspirate the sample when the analyte sample container 8 on the sample disk 3 is at an analyte sampling position 10. The sample dispensing probe 9 can dispense the sample when the reaction container 7 on the reaction disk 2 and a reaction container 12 of the blood coagulation time analysis unit U are at a sample dispensing position 11.

A first reagent dispensing probe 13 is disposed between the first reagent disk 4 and the reaction disk 2, and a second reagent dispensing probe 14 is disposed between the second reagent disk 5 and the reaction disk 2. The first reagent dispensing probe 13 and the second reagent dispensing probe 14 can rotate about respective axes thereof, and aspirating positions and dispensing positions of a first reagent and a second reagent are present on respective rotation orbits thereof.

The first reagent dispensing probe 13 and the second reagent dispensing probe 14 can aspirate the reagents when the reagent containers are at the aspirating positions on the first reagent disk 4 and the second reagent disk 5. The first reagent dispensing probe 13 and the second reagent dispensing probe 14 can dispense the reagent when the reaction container 7 is at one of the dispensing positions on the reaction disk 2.

The barcode reader R is installed at the sample disk 3. The barcode reader R reads a barcode attached to the analyte sample container 8 placed on the sample disk 3 under control of a barcode reader control unit 109 to be described below. A position and a sample aspirating schedule of the analyte sample container 8 whose barcode is read are managed by a computer.

The blood coagulation time analysis unit U includes a blood coagulation time detection unit U1, a blood coagulation reagent dispensing probe U2, a disposable reaction container magazine U3, a reaction container transfer mechanism U4, and a reaction container disposal port U5. A detailed configuration of the blood coagulation time detection unit U1 will be described below.

[Control System and Signal Processing System of Automatic Analyzer]

Next, a control system and a signal processing system of the automatic analyzer 1 will be briefly described. The automatic analyzer 1 is electrically connected to control units that control the various hardware described above. The control units transmit control signals based on a setting input from the operation unit 200.

The operation unit 200 has a configuration in which an input device 201, a printer 202, a computer 203, a memory 204, a display unit 205, and an external output medium 206 are connected via an interface 207.

The input device 201 is configured with, for example, a keyboard for inputting an operation instruction or the like. The printer 202 performs printing, for example, when a measurement result is to be output as a report or the like.

The memory 204 includes, for example, a random access memory (RAM), a read only memory (ROM), and a solid state drive (SSD). In the RAM, for example, information indicating a position of an analyte sample at the time when a sample disk control unit 108 causes the sample disk 3 to rotate is recorded. In addition, in the RAM, information indicating an analysis state of the analyte sample at the time when a sample dispensing control unit 101 to be described below causes the sample dispensing probe 9 to aspirate the analyte sample is recorded. In the ROM, for example, a program to be executed by the computer 203 is recorded. In the SSD and the external output medium 206, for example, a measurement result is recorded.

In the display unit 205, the measurement result and states of the sample disk 3 and the analyte sample container are displayed. The display unit 205 is configured with, for example, a liquid crystal display or a CRT display.

The computer 203 is connected, via the interface 207, to the sample dispensing control unit 101, a first reagent dispensing control unit 102, a second reagent dispensing control unit 103, a blood coagulation reagent dispensing control unit 104, a first A/D converter 105, a second A/D converter 106, a transfer mechanism control unit 107, the sample disk control unit 108, and the barcode reader control unit 109, and transmits electrical signals for instructions to the control units.

The sample dispensing control unit 101 controls a sample dispensing operation of the sample dispensing probe 9 based on an instruction received from the computer 203.

The first reagent dispensing control unit 102 and the second reagent dispensing control unit 103 control reagent dispensing operations of the first reagent dispensing probe 13 and the second reagent dispensing probe 14 based on instructions received from the computer 203.

The transfer mechanism control unit 107 controls the reaction container transfer mechanism U4 based on an instruction received from the computer 203, and transports the disposable reaction container 12 for blood coagulation analysis between the reaction container magazine U3, the sample dispensing position 11, a reaction port of the blood coagulation time detection unit U1, and the reaction container disposal port U5.

The blood coagulation reagent dispensing control unit 104 controls the blood coagulation reagent dispensing probe U2 based on an instruction received from the computer 203, and dispenses a blood coagulation reagent to the analyte sample-containing reaction container 12 placed at the reaction port.

Alternatively, the blood coagulation reagent dispensing control unit 104 dispenses a pretreatment liquid, which is a liquid mixture contained in the reaction container 7 of the sample and the first reagent for blood coagulation analysis, to an empty reaction container 12 with the blood coagulation reagent dispensing probe U2. In this case, the blood coagulation reagent dispensing probe U2 dispenses the second reagent for blood coagulation analysis to the reaction container 12 containing the pretreatment liquid. Here, the reagents for blood coagulation analysis are placed on the first reagent disk 4 and the second reagent disk 5, and are used for blood coagulation analysis once being dispensed into the reaction container 7 on the reaction disk 2 as necessary by the first reagent dispensing probe 13 and the second reagent dispensing probe 14.

A photometric value of transmitted light or scattered light of light irradiated to a reaction liquid in the reaction container 7 for biochemical analysis is converted into a digital signal by the first A/D converter 105 and is taken into the computer 203. A photometric value of transmitted light or scattered light of light irradiated to the reaction liquid in the reaction container 12 for blood coagulation analysis is converted into a digital signal by the second A/D converter 106 and is taken into the computer 203.

[Analytical Procedure]

Analysis of biochemical items performed by the automatic analyzer 1 is performed in the following procedure. First, after an operator places the analyte sample container 8 on the sample disk 3, the barcode reader control unit 109 causes the barcode reader R to read a barcode of the analyte sample container 8. The operator uses the input device 201 such as a keyboard to input examination items for each sample whose barcode is read.

The sample disk control unit 108 moves the analyte sample container 8 to the analyte sampling position 10 in accordance with an analysis parameter. The sample dispensing probe 9 moves to the analyte sampling position 10 under control of the sample dispensing control unit 101, and dispenses a predetermined amount of sample to the reaction container 7 for biochemical analysis.

The reaction container 7 for biochemical analysis to which the sample is dispensed is transferred by the rotation of the reaction disk 2 and stopped at a reagent receiving position. The first reagent dispensing control unit 102 and the second reagent dispensing control unit 103 cause the first reagent dispensing probe 13 and the second reagent dispensing probe 14 to dispense a predetermined amount of reagent solution into the reaction container 7 for biochemical analysis in accordance with the analysis parameter input in advance. In contrast to the above description, the reagent may be dispensed into the reaction container 7 earlier than the sample.

Thereafter, the sample and the reagent are agitated by an agitating mechanism (not shown) and mixed. When the reaction container 7 for biochemical analysis crosses a photometric position, transmitted light or scattered light of light irradiated to the reaction liquid is measured by the photometer. The measured transmitted light or scattered light is converted into data of a numerical value proportional to a light amount by the first A/D converter 105, and is taken into the computer 203 via the interface 207.

By using the numerical value, concentration data is calculated based on a calibration curve measured in advance by an analysis method specified for each examination item. Component concentration data as an analysis result of each inspection item is output to the printer 202 or a screen of the display unit 205.

Before the above measurement operations are performed, the operator may set various parameters required for the analysis and register the reagent and the sample, via an operation screen of the display unit 205. In addition, the operator can check the analysis result after the measurement, using the operation screen on the display unit 205.

Analysis of a blood coagulation time item performed by the automatic analyzer 1 is performed mainly in the following procedure. First, the operator uses the input device 201 such as a keyboard to input examination items for each sample. The reaction container transfer mechanism U4 transfers the disposable reaction container 12 for blood coagulation analysis from the reaction container magazine U3 to the sample dispensing position 11.

The sample disk control unit 108 moves the analyte sample container 8 to the analyte sampling position 10 in accordance with an analysis parameter. The sample dispensing probe 9 moves to the analyte sampling position 10 and dispenses a predetermined amount of the sample into the reaction container 12 for blood coagulation analysis.

The reaction container 12 for blood coagulation analysis to which the sample is dispensed is transferred to the reaction port of the blood coagulation time detection unit U1 by the reaction container transfer mechanism U4, and is heated to a predetermined temperature. The first reagent dispensing probe 13 dispenses a predetermined amount of reagent solution into the reaction container 7 for biochemical analysis on the reaction disk 2 in accordance with the analysis parameter of the corresponding examination item.

Since a thermostatic bath (not shown) is provided at the reaction disk 2, the reagent solution dispensed into the reaction container 7 for biochemical analysis is heated to 37° C. After the reagent is heated to the predetermined temperature, the blood coagulation reagent dispensing probe U2 aspirates the reagent contained in the reaction container 7 for biochemical analysis and dispenses the reagent to the reaction container 12 for blood coagulation analysis.

Photometry of transmitted light or scattered light of light irradiated to the reaction container 12 for blood coagulation analysis is started from a time point when the reagent is dispensed. The measured transmitted light or scattered light is converted into data of a numerical value proportional to a light amount by the second A/D converter 106, and is taken into the computer 203 via the interface 207.

The computer 203 uses the converted numerical value to obtain a time required for the blood coagulation reaction (hereinafter, simply referred to as blood coagulation time). For example, for an examination item such as activated partial thromboplastin time (ATPP), the blood coagulation time obtained as described above is output as an analysis result. For examination items such as fibrinogen (Fbg), with respect to the obtained blood coagulation time, further component concentration data is obtained based on a calibration curve measured in advance by an analysis method specified for each examination item, and then is output as an analysis result.

The blood coagulation time and the component concentration data, as the analysis results of each examination item, are output to the printer 202 or the screen of the display unit 205. Here, before the above measurement operation is performed, the operator sets the various parameters required for analysis, and registers the reagent and the sample in advance via the operation screen of the display unit 205. In addition, the operator can check the analysis result after the measurement using the operation screen on the display unit 205.

A dispensing destination of the sample dispensed by the sample dispensing probe 9 may be the reaction container 7 for biochemical analysis. In this case, the sample can be dispensed into the reaction container 12 for blood coagulation analysis, using the blood coagulation reagent dispensing probe U2 after reacting with the pretreatment liquid in the reaction container 7 for biochemical analysis in advance as described above.

The blood coagulation reagent dispensing probe U2 mixes the reagent with the sample, which is previously contained in the reaction container 12 for blood coagulation analysis, by momentums generated at the time when the reagent is dispensed. This mixing method is called dispensing agitation. In contrast to the above examples, the dispensing order of the sample and reagent may be dispensing the reagent earlier than dispensing the sample. In this case, the reagent and the sample can be mixed by the momentums generated at the time when the sample is dispensed.

Here, when the dispensing agitation is to be performed, it is important to improve positioning accuracy of a tip end of the blood coagulation reagent dispensing probe U2 in order to perform sufficient agitation.

[Light Shielding Cover]

Figure 2:
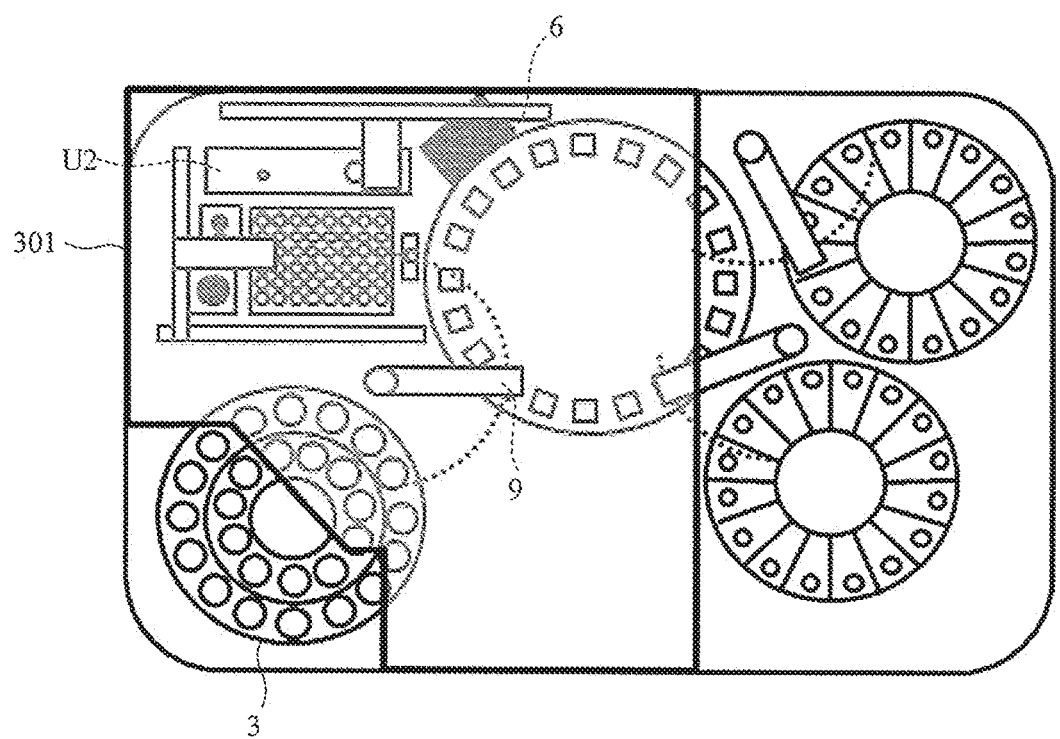
FIG. 2 is a diagram illustrating a cover range on a biochemical analysis unit.

FIG. 2 is a diagram illustrating a cover range over the biochemical analysis unit 100. Here, an example of the complex automatic analyzer 1, which includes the turntable type biochemical analysis unit 100 and the blood coagulation time analysis unit U, will be described.

As illustrated in FIG. 2, the photometer 6 and the blood coagulation time detection unit U1 of the automatic analyzer 1 are required to be shielded from light. In addition, the sample disk 3 includes a sample guard for avoiding risks such as droplet dropping from the sample dispensing probe 9. Therefore, a light shielding cover 301 including a cover that shields light and a sample guard is attached to the biochemical analysis unit 100. The operator is required to place the analyte sample onto the sample disk 3 or remove the analyte sample from the sample disk 3 in an area not covered by the light shielding cover 301.

[Analyte Status Display Screen]

A processor of the computer 203 functions as, for example, the sample information output unit 208 by executing a program recorded in the memory 204. The sample information output unit 208 acquires analysis information indicating the analysis state of each analyte sample placed on the sample disk 3 and position information indicating the position of each analyte sample, and displays the analysis information, the position information, and an image indicating the light shielding cover on the display unit 205 in a manner superimposed on one another.

Figure 3:
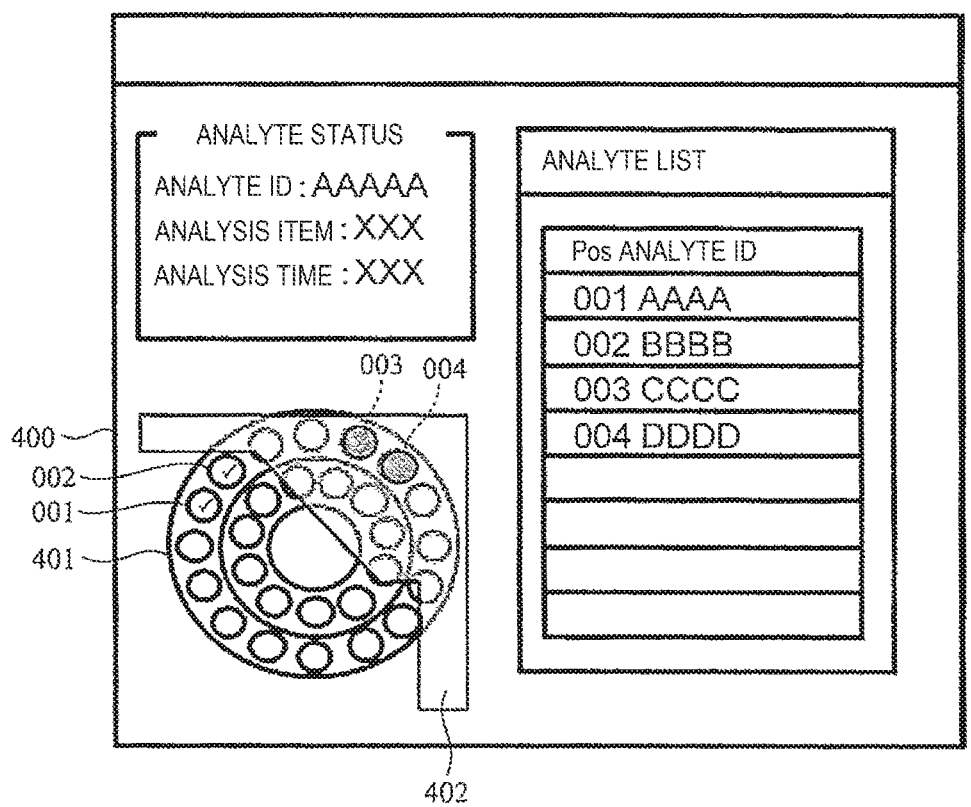
FIG. 3 is a diagram illustrating an example of a sample status screen displayed on a display unit.

FIG. 3 is a diagram illustrating an example of an analyte status screen displayed on the display unit 205. An analyte status screen 400 in the present drawing displays an analyte status, a sample list, and sample disk monitor information 401.

In the sample status, for example, an analyte ID, an analysis item, and an analysis time of a specified analyte sample container are displayed. In the sample list, an ID of an analyte sample registered by the operator to be analyzed is displayed.

The sample disk monitor information 401 is, for example, an image of computer graphics indicating a state of the sample disk 3. On the sample disk monitor information 401, an image of computer graphics indicating the light shielding cover 301 is superimposed as a light shielding cover area 402.

As illustrated in FIG. 3, the sample information output unit 208, for example, superimposes the light shielding cover area 402 on the display unit 205 in a transparent color, and visibly displays analysis states of analyte samples positioned in an area overlapping the light shielding cover 301. In this way, the operator can check whether the analyte sample container 8 is present below the light shielding cover 301. When the analyte sample container 8 is present below the light shielding cover 301, the operator can predict how much the sample disk 3 is required to rotate to remove the analyte sample container 8.

In the sample disk monitor information 401, it is displayed at a position of which number of the sample disk 3 the analyte sample container 8 is placed. In the example illustrated in FIG. 3, the analyte sample containers 8 are placed at four positions, among which two positions 001 and 002 are attached with check marks and the other two positions 003 and 004 are painted out. For example, an analyte sample, whose placement position of the analyte sample container 8 is marked with the check mark, indicates an analyzed analyte sample, and an analyte sample, whose placement position of the analyte sample container 8 is painted out, indicates an analyte sample that is not analyzed.

That is, the sample information output unit 208 displays analyte samples whose analysis is completed and analyte samples whose analysis is not completed in different states among the analyte samples. In this manner, the operator can understand which analyte sample is analyzed. Hereinafter, a mechanism in which the sample information output unit 208 changes the display of the sample disk monitor information together with analysis progress of the analyte sample will be described.

[Change of Sample Disk and of Sample Disk Monitor Information]

FIG. 4 is a diagram illustrating changes of the sample disk 3 and of the sample disk monitor information 401. 3-1 to 3-4 illustrated on the left side are numeral signs indicating actual states of the sample disk 3 provided in the biochemical analysis unit 100, and 401-1 to 401-4 illustrated on the right side are numeral signs indicating states of the sample disk monitor information 401.

First, the operator places the analyte sample containers 8 at positions of numbers 10 to 15 of the sample disk 3, and inputs the analyte sample containers 8 as analysis targets (state 3-1). When the operator presses a start button, the barcode reader R reads barcodes labeled on the analyte sample containers 8 of numbers 10 to 15. Then, container placement positions of numbers 10 to 15 are painted out in the sample disk monitor information 401 (state 401-1a).

When the barcode reader R finishes reading the barcodes, the sample disk control unit 108 rotates the sample disk 3 until a position of the analyte sample container 8 placed at number 10 reaches the analyte sampling position 10 (state 3-2). When the sample dispensing probe 9 finishes aspirating the sample from the analyte sample container 8, in the sample disk monitor information 401, the position of the analyte sample container 8 at number 10 is changed from being painted out to being check-marked (state 401-2a).

The sample disk control unit 108 and the sample dispensing probe 9 repeat the above operations until aspiration of the analyte sample placed at the position of number 15 is finished. When aspiration of the analyte sample placed at the position of number 15 is finished, the automatic analyzer 1 enters a standby state, and the sample disk 3 is stopped in a state in which the position of number 15 coincides with the analyte sampling position 10. In this case, since the analyte sample containers 8 placed at the positions of numbers 10 to 15 are still present below the light shielding cover 301, the operator cannot remove the analyte sample containers 8.

When the operator further places another analyte sample container 8 at a position of number 1 and presses the start button again in this state, a barcode of the analyte sample container 8 placed at the position of number 1 is read, and the sample disk 3 is rotated until the position of number 1 coincides with the analyte sampling position 10 (state 3-3). When the position of number 1 coincides with the analyte sampling position 10, the analyte sample containers 8 of the positions of numbers 10 to 13 are at a removable position which is not covered by the light shielding cover 301 (state 401-3a).

When the operator further places the analyte sample container 8 at the position of number 12 and presses the start button again after aspiration of the analyte sample of the position of number 1 is finished, the barcode of the analyte sample container 8 placed at the position of number 12 is read, and the sample disk 3 is rotated until the position of number 12 coincides with the analyte sampling position 10 (state 3-4). The position of number 12 is at the same position as the analyte sampling position 10, and is displayed in a painted state in the sample disk monitor information 401 (state 401-4a). As illustrated in the sample disk monitor information 401 of state 401-4a, the positions of the analyte sample containers 8 whose analyte samples are aspirated are marked with check marks regardless of whether the operator has removed the analyte sample containers 8.

As described above, each time the sample disk control unit 108 performs the rotation operation of the sample disk or each time the sample dispensing probe 9 performs the aspiration, the sample information output unit 208 updates the information indicating the position of the analyte sample container 8 or the information indicating the analysis state of the analyte sample, and displays the sample disk monitor information 401. In this way, every time the sample disk control unit 108 rotates the sample disk 3 or the sample dispensing probe 9 finishes the dispensing of one analyte sample container 8, the operator can check the latest state in the sample disk monitor information 401.

[Sample Dispensing Flow]

Figure 5:
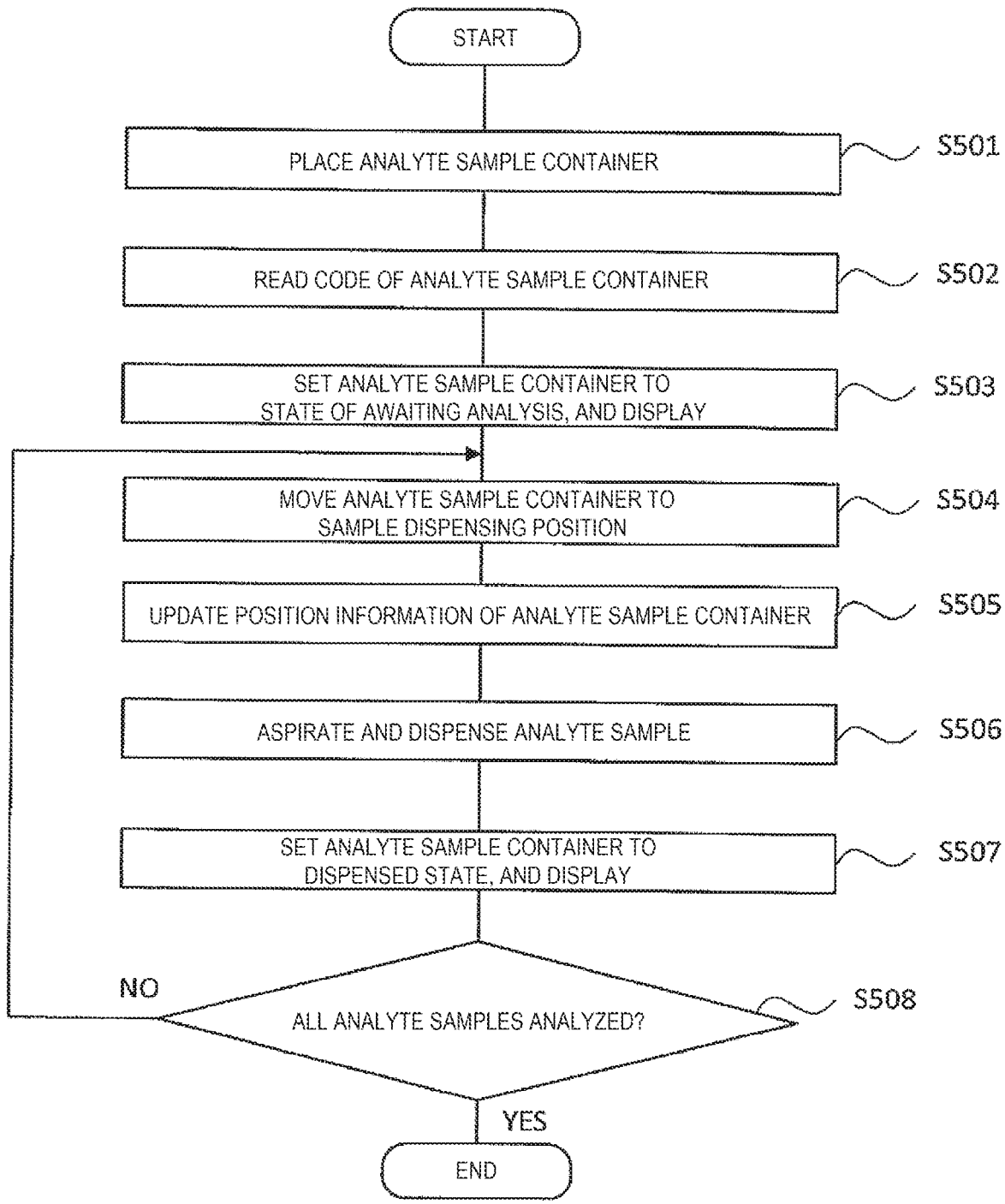
FIG. 5 is a flowchart illustrating a sample dispensing flow.

FIG. 5 is a flowchart illustrating a sample dispensing flow. First, the user places the sample container 8 on the sample disk (S501). Subsequently, the barcode reader control unit 109 controls the barcode reader R to read the barcode attached to the analyte sample container 8 (S502). Then, the sample information output unit 208 causes the display unit 205 to display the sample disk monitor information 401, with a placement position of the analyte sample container 8 whose barcode is read set to a state of awaiting analysis (S503).

Subsequently, the sample disk control unit 108 rotates the sample disk 3 until the position of the analyte sample container 8 coincides with the analyte sampling position 10 (S504). Then, the sample information output unit 208 updates the position information of the analyte sample container 8 in the sample disk monitor information 401 (S505).

Subsequently, the sample dispensing probe 9 aspirates an analyte sample that is at the analyte sampling position 10 and dispenses the analyte sample into a reaction container (S506). Then, the sample information output unit 208 updates an analysis state of the analyte sample container 8 in the sample disk monitor information 401 to an aspirated state (or a dispensed state) (S507).

When analysis of all the analyte samples is finished (YES in S508), the automatic analyzer 1 ends the analysis of the analyte sample. When the analysis of all analyte samples is not finished (NO in step S508), the automatic analyzer 1 returns the process to step S504 and repeats the same operations for the remaining analyte sample containers 8.

Modification

The sample information output unit 208 may display in a highlighted manner an analyte sample that can be removed from the sample disk 3 among analyte samples listed in the sample list.

Figure 6:
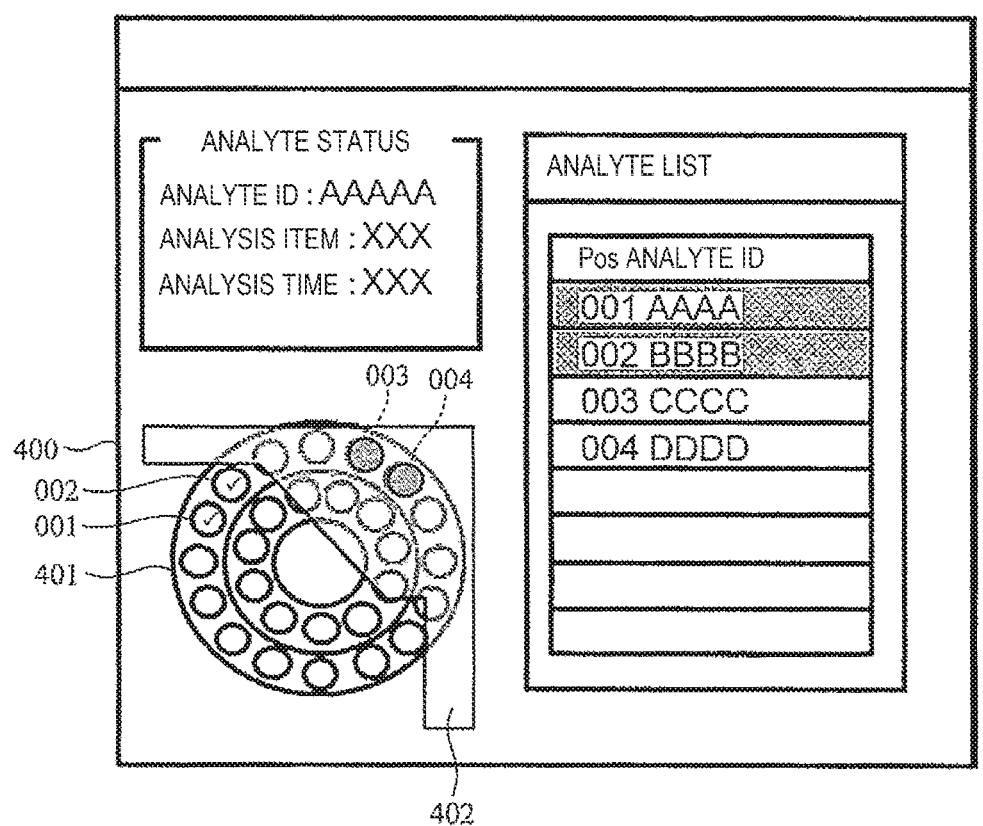
FIG. 6 is a diagram illustrating another example of the sample status screen.

FIG. 6 is a diagram illustrating another example of the sample status screen. In the example illustrated in FIG. 6, the analyte sample containers placed at the positions of the numbers 001 and 002 which are marked with check marks are in a removable state, and the labels of the analyte samples of the numbers 001 and 002 in the sample list are painted out and displayed in a highlighted manner. In this way, the operator can easily grasp which analyte sample container 8 is removable. In addition, since the ID of the removable sample container 8 can be grasped, the operator can also grasp which sample is finished in being analyzed.

The invention is not limited to the above embodiments, and includes various modifications. For example, the above embodiments have been described in detail for easy understanding of the invention, and the invention is not necessarily limited to those including all the configurations described. A part of the configuration of one embodiment can be replaced with the configuration of another embodiment, and the configuration of another embodiment can be added to the configuration of one embodiment. A part of the configuration of one embodiment may be added, deleted, or replaced with another configuration. A part or all of the above configurations, functions, processing units, processing means, and the like may be implemented by hardware, for example, through designing an integrated circuit. The above configurations, functions, and the like may also be implemented by software by means of interpreting and executing a program, by a processor, for implementing respective functions. Information such as a program, a table, or a file that implements each function can be stored in a recording device such as a memory, a hard disk or an SSD, or in a recording medium such as an IC card, an SD card, or a DVD.

REFERENCE SIGN LIST 1 automatic analyzer
2 reaction disk
3 sample disk
4 first reagent disk
5 second reagent disk
6 photometer
7 reaction container for biochemical analysis
8 analyte sample container
9 sample dispensing probe
10 analyte sampling position
11 sample dispensing position
12 reaction container
13 first reagent dispensing probe
14 second reagent dispensing probe
U blood coagulation time analysis unit
U1 blood coagulation time detection unit
U2 blood coagulation reagent dispensing probe
U3 disposable reaction container magazine
U4 reaction container transfer mechanism
U5 reaction container disposal port
100 analysis unit
101 sample dispensing control unit
102 first reagent dispensing control unit
103 second reagent dispensing control unit
104 blood coagulation reagent dispensing control unit
105 first A/D converter
106 second A/D converter
107 transfer mechanism control unit
108 sample disk control unit
200 operation unit
201 input device
202 printer
203 computer
204 memory
205 display unit
206 external output medium
207 interface
208 sample information output unit
301 light shielding cover
400 analyte status screen
401 sample disk monitor information
402 light shielding cover area display
403 in-analysis state
404 analysis-completed state

The invention claimed is:

1. An automatic analyzer, comprising:
a sample disk on which an analyte sample container containing an analyte sample is to be placed;
a sample disk control unit configured to control rotation of the sample disk; a sample dispensing probe configured to aspirate the analyte sample from the analyte sample container when the analyte sample container reaches a predetermined aspirating position by rotation of the sample disk;
a photometer configured to perform automatic biochemical analysis; a blood coagulation time detection unit configured to perform blood coagulation time analysis;
a light shielding cover configured to cover the photometer and the blood coagulation time detection unit; and
a computer configured to output information on the analyte sample; and
a display unit configured to display analysis information, wherein
the computer is configured to acquire the analysis information indicating an analysis state of the analyte sample placed on the sample disk of whether the analyte sample has been analyzed and position information indicating a rotation position of the analyte sample according to rotation of the sample disk based on a position of the analyte sample placed on the sample disk, and to display the analysis information, the position information, and an image showing the light shielding cover on the display unit in a manner superimposed on one another during an analysis operation of the automatic analyzer including the automatic biochemical analysis and the blood coagulation time analysis;
the computer is further configured to superimpose the light shielding cover on the display unit in a transparent color, and to visibly display on the display the analysis state of the analyte sample when the analyte sample is positioned in an area overlapping the light shielding cover; and
the computer is further configured to further display on the display a list of analyte samples placed on the sample disk, and to display in a highlighted manner an analyte sample that can be removed from the sample disk among the analyte samples listed in the list.

2. The automatic analyzer according to claim 1, wherein the computer is further configured to update information indicating the position of the analyte sample each time the sample disk control unit performs a rotation operation of the sample disk.

3. The automatic analyzer according to claim 1, wherein computer is configured to display an analyte sample whose analysis is completed and an analyte sample whose analysis is not completed in different states in an image showing the analyte samples.

4. An image processing method of an automatic analyzer, wherein
the automatic analyzer includes:
a sample disk on which an analyte sample container containing an analyte sample is to be placed;
a sample disk control unit configured to control rotation of the sample disk;
a sample dispensing probe configured to aspirate the analyte sample from the analyte sample container when the analyte sample container reaches a predetermined aspirating position by rotation of the sample disk;
a photometer configured to perform automatic biochemical analysis;
a blood coagulation time detection unit configured to perform blood coagulation time analysis; and
a light shielding cover configured to cover the photometer and the blood coagulation time detection unit,
a display unit configured to display analysis information, and
the image processing method comprising:
a step of acquiring analysis information indicating an analysis state of the analyte sample placed on the sample disk of whether the analyte sample has been analyzed and position information indicating a rotation position of the analyte sample according to rotation of the sample disk based on a position of the analyte sample placed on the sample disk;

a step of displaying the analysis information on the display, the position information, and an image indicating the light shielding cover on a display unit in a manner superimposed on one another during an analysis operation of the automatic analyzer including the automatic biochemical analysis and the blood coagulation time analysis;

a step of superimposing the light shielding cover on the display unit in a transparent color, and to visibly display the analysis state of the analyte sample when the analyte sample is positioned in an area overlapping the light shielding cover; and a step to further display on the display a list of analyte samples placed on the sample disk, and to display in a highlighted manner an analyte sample that can be removed from the sample disk among the analyte samples listed in the list.

\* \* \* \* \*